(12) United States Patent
Ritter

(10) Patent No.: US 7,345,195 B1
(45) Date of Patent: **\*Mar. 18, 2008**

(54) PROCESS FOR THE SYNTHESIS OF 2,5-DIHYDROXYTEREPHTHALIC ACID

(75) Inventor: Joachim C. Ritter, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/604,938

(22) Filed: Nov. 28, 2006

(51) Int. Cl.
*C07C 63/00* (2006.01)
(52) U.S. Cl. ...................... 562/405; 562/400
(58) Field of Classification Search ............... 562/405, 562/400
See application file for complete search history.

(56) References Cited

U.S. PATENT DOCUMENTS

| | | | |
|---|---|---|---|
| 3,047,536 | A | 7/1962 | Gordon |
| 3,227,680 | A | 1/1966 | Tamblyn et al. |
| 3,894,079 | A | 7/1975 | Knobloch |
| 3,932,542 | A | 1/1976 | Gerns |
| 4,030,933 | A | 6/1977 | Conciatori |
| 5,674,969 | A | 10/1997 | Sikkema et al. |
| 5,703,264 | A | 12/1997 | Yoshida |
| 5,703,274 | A | 12/1997 | Gelmont |
| 6,245,929 | B1 | 6/2001 | Soloveichik |

FOREIGN PATENT DOCUMENTS

| | | |
|---|---|---|
| AT | 265244 | 10/1968 |
| AU | 265244 | 10/1964 |
| DE | 1812703 A1 | 8/1969 |
| GB | 1238224 | 7/1971 |
| IL | 112706 | 4/1998 |
| WO | WO 2006/104974 A1 | 10/2006 |

OTHER PUBLICATIONS

U.S. Appl. No. 60/665,737, filed Mar. 28, 2005, Steven R. Allen et al.
U.S. Appl. No. 11/604,936, Ritter.
U.S. Appl. No. 11/604,937, Ritter.
U.S. Appl. No. 11/604,935, Ritter.
U.S. Appl. No. 11/604,939, Ritter.
U.S. Appl. No. 11/604,940, Ritter.
U.S. Appl. No. 11/604,941, Ritter.
U.S. Appl. No. 11/604,942, Ritter.

Adolf Marzin, 2,5-Dibromotoluic Acid, Journal Fuer Praktische Chemie, 1933, pp. 103-106.
Tara Singh et. al., Di-Xanthones. Part I. Chromono-2':3'-2:3-Xanthone, Jour. Indian Chem. Soc., 1957, vol. 34:321-323.
Irena Rusonik et. al., CU(I)(2,5,8,11-Tetramethyl-2,5,8,11-Tetraazadodecane)+ as a Catalyst for Ullmann's Reaction, Dalton Transactions, pp. 2024-2028, 2003.
Rolando F. Pellon Comdom et. al., Synthesis of Salicyclic Acid Derivatives From the Corresponding 2-Chlorobenzoic Acid Using Water as Solvent, Synthetic Communications, 2002, vol. 32:2055-2059.
J. E. McIntyre et. al., The Oxidation of Alkylaromatic Compounds in Aqueous Hydrogen Bromide., Journal of the Chemical Society, Abstracts, 1961, pp. 4082-4085.
F. F. Shcherbina et. al., Liquid-Phase Oxidation of 2,5-Dicholoro-P-Xylene, Zhurnal Prikladnoi Khimii, Sankt-Peterburg, Russian Federation, 1990, vol. 63:467-470.
Robert J. Perry et. al., Synthesis of Polyimides via the Palladium-Catalyzed Carbonylation of Bis(O-Iodo Esters) and Diamines, Macromolecules, 1995, vol. 28:3509-3515.
Magal Saphier et al., Copper(I) as a Homogeneous Catalyst for the Ullmann Reaction in Aqueous Solution—the Transformation of 2-Bromobenzoate Into Salicylate.
Mark Gelmont et. al., A New Route for the Preparation of 5-Hydroxyisophthalic Acid, Organic Process Research & Development, 2002, vol. 6:591-596.
Yoel Sasson et. al., Liquid-Phase Oxidation of Deactivated Methylbenzenes by Aqueous Sodium Hypochlorite Catalyzed by Ruthenium Salts Under Phase-Transfer, Journal of Organic Chemistry, 1986, vol. 51:2880-2883.
Ruggli and Brandt, A New Linear Benzodipicoline, 2,6-Dimethyl-1,5-anthrazoline, 51st Communication Concerning Nitrogen Heterocycles, Basel University Institute for Organic Chemistry, Basel, Switzerland, Jan. 6, 1944.
Kevin W. Anderson et al, The Selective Reaction of Aryl Halides with KOH: Synthesis of Phenols, Aromatic Ethers, and Benzofurans; J. Am. Chem. Soc. 2006, 128, 10694-10695, American Chemical Society, New York NY.
M. Lammers et al, Mechanical Properties and Structural Transitions in the New Rigid-Rod Polymer Fibre PIPD ("M5") During the Manufacturing Process, Polymer, vol. 39, No. 24, 1998, 5999-6005, Elsevier, New York NY.
Doetze J. Sikkema, Design, Synthesis and Properties of a Novel Rigid Rod Polymer, PIPD or "M5": High Modulus and Tenacity Fibres with Substantial Compressive Strength, Polymer, vol. 39, No. 24, 1998, pp. 5981-5986, Elsevier, New York, NY.
Doetze J. Sikkema, Manmade Fibers One Hundred Years: Polymers and Polymer Design, Journal of Applied Polymer Science, vol. 83, 484-488, 2002, John Wiley & Sons, Inc., New York NY.

*Primary Examiner*—Yvonne Eyler
*Assistant Examiner*—Sudhakar Katakam

(57) ABSTRACT

2,5-dihydroxyterephthalic acid is produced in high yields and high purity from 2,5-dihaloterephthalic acid by contact with a copper source and a ligand that coordinates to copper under basic conditions.

15 Claims, No Drawings

PROCESS FOR THE SYNTHESIS OF 2,5-DIHYDROXYTEREPHTHALIC ACID

TECHNICAL FIELD

This invention relates to the manufacture of hydroxybenzoic acids, which are valuable for a variety of purposes such as use as intermediates or as monomers to make polymers.

BACKGROUND

Hydroxybenzoic acids are useful as intermediates in the manufacture of many valuable materials including pharmaceuticals and compounds active in crop protection, and are also useful as monomers in the production of polymers. In particular, 2,5-dihydroxyterephthalic acid (Formula I, "DHTA") is a useful monomer for the synthesis of high strength fibers such as those made from poly[(1,4-dihydrodiimidazo[4,5-b:4',5'-e]pyridine-2,6-diyl) (2,5-dihydroxy-1,4-phenylene)].

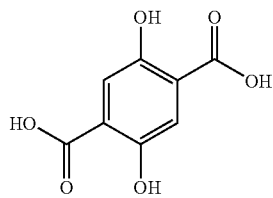

Various preparations of 2,5-dihydroxyterephthalic acid and other hydroxybenzoic acids are known. Marzin, in *Journal fuer Praktische Chemie*, 1933, 138, 103-106, teaches the synthesis of 2,5-dihydroxyterephthalic acid from 2,5-dibromoterephthalic acid (Formula II, "DBTA") in the presence of copper powder.

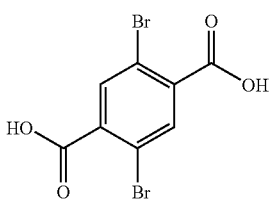

Singh et al, in *Jour. Indian Chem. Soc.*, Vol. 34, No. 4, pages 321-323 (1957), report the preparation of a product that includes DHTA by the condensation of DBTA with phenol in the presence of KOH and copper powder.

Rusonik et al, *Dalton Transactions*, 2003, 2024-2028, describe the transformation of 2-bromobenzoic acid into salicylic acid, benzoic acid, and diphenoic acid in a reaction catalyzed by Cu(I) in the presence of various ligands. A tertiary tetraamine minimizes the formation of diphenoic acid in use with Cu(I).

Comdom et al, *Synthetic Communications*, 32(13), 2055-59 (2002), describe a process for the synthesis of salicylic acids from 2-chlorobenzoic acids. Stoichiometric amounts of pyridine (0.5 to 2.0 moles per mole of 2-chlorobenzoic acid) are used such as at least 1.0 mole pyridine per mole 2-chlorobenzoic acid. Cu powder is used as a catalyst along with the pyridine.

The various prior art processes for making hydroxybenzoic acids are characterized by long reaction times, limited conversion resulting in significant productivity loss, or the need to run under pressure and/or at higher temperatures (typically 140 to 250° C.) to get reasonable rates and productivity. A need therefore remains for a process by which 2,5-dihydroxy terephthalic acid can be produced economically; with low inherent operational difficulty; and with high yields and high productivity in both small- and large-scale operation, and in batch and continuous operation.

SUMMARY

One embodiment of this invention provides a process for preparing 2,5-dihydroxyterephthalic acid by (a) contacting a 2,5-dihaloterephthalic acid (III)

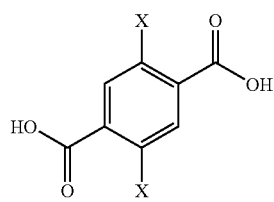

where X=Cl, Br, or I
with base in water to form therefrom the corresponding dibasic salt of 2,5-dihaloterephthalic acid; (b) contacting the dibasic salt of 2,5-dihaloterephthalic acid with base in water, and with a copper source in the presence of a ligand that coordinates to copper, to form the dibasic salt of 2,5-dihydroxyterephthalic acid from the dibasic salt of 2,5-dihaloterephthalic acid at a solution pH of at least about 8; (c) optionally, separating the dibasic salt of 2,5-dihydroxyterephthalic acid from the reaction mixture in which it is formed; and (d) contacting the dibasic salt of 2,5-dihydroxyterephthalic acid with acid to form therefrom 2,5-dihydroxyterephthalic acid.

Yet another embodiment of this invention provides a process for preparing a 2,5-dialkoxyterephthalic acid by preparing a 2,5-dihydroxyterephthalic acid in the manner described above and then converting the 2,5-dihydroxyterephthalic acid to a 2,5-dialkoxyterephthalic acid.

Yet another embodiment of this invention consequently provides a process for preparing 2,5-dialkoxyterephthalic acid by (a) contacting a 2,5-dihaloterephthalic acid (III)

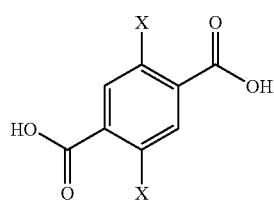

where X=Cl, Br, or I
with base in water to form therefrom the corresponding dibasic salt of 2,5-dihaloterephthalic acid; (b) contacting the dibasic salt of 2,5-dihaloterephthalic acid with base in water, and with a copper source in the presence of a ligand that coordinates to copper, to form the dibasic salt of 2,5-dihydroxyterephthalic acid from the dibasic salt of 2,5-dihaloterephthalic acid at a solution pH of at least about 8; (c) optionally, separating the dibasic salt of 2,5-dihydroxyterephthalic acid from the reaction mixture in which it is formed; (d) contacting the dibasic salt of 2,5-dihydroxyterephthalic acid with acid to form therefrom a 2,5-dihydroxyterephthalic acid; and (e) converting the 2,5-dihydroxyterephthalic acid to a 2,5-dialkoxyterephthalic acid.

Yet another embodiment of this invention provides a process for preparing a 2,5-dihydroxyterephthalic acid or a 2,5-dialkoxyterephthalic acid as described above that further includes a step of subjecting the 2,5-dihydroxyterephthalic acid or the 2,5-dialkoxyterephthalic acid to a reaction to prepare therefrom a compound, monomer, oligomer or polymer.

Yet another embodiment of this invention consequently provides a process for preparing a compound, monomer, oligomer or polymer by (a) contacting a 2,5-dihaloterephthalic acid (III)

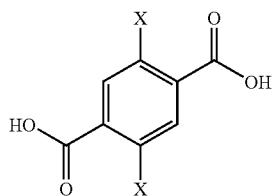

III where X=Cl, Br, or I with base in water to form therefrom the corresponding dibasic salt of 2,5-dihaloterephthalic acid; (b) contacting the dibasic salt of 2,5-dihaloterephthalic acid with base in water, and with a copper source in the presence of a ligand that coordinates to copper, to form the dibasic salt of 2,5-dihydroxyterephthalic acid from the dibasic salt of 2,5-dihaloterephthalic acid at a solution pH of at least about 8; (c) optionally, separating the dibasic salt of 2,5-dihydroxyterephthalic acid from the reaction mixture in which it is formed; (d) contacting the dibasic salt of 2,5-dihydroxyterephthalic acid with acid to form therefrom 2,5-dihydroxyterephthalic acid; (e) optionally, converting the 2,5-dihydroxyterephthalic acid to a 2,5-dialkoxyterephthalic acid; and (f) subjecting the 2,5-dihydroxyterephthalic acid and/or the 2,5-dialkoxyterephthalic acid to a reaction to prepare therefrom a compound, monomer, oligomer or polymer.

In yet another embodiment, the ligand in one or more of the processes described herein may be a diketone.

DETAILED DESCRIPTION

This invention provides a high yield and high productivity process for preparing a 2,5-dihydroxyterephthalic acid by contacting a 2,5-dihaloterephthalic acid with base to form the dibasic salt of 2,5-dihaloterephthalic acid; contacting the dibasic salt of 2,5-dihaloterephthalic acid with base, and with a copper source in the presence of a ligand that coordinates to copper, to form the dibasic salt of 2,5-dihydroxyterephthalic acid; and then contacting the dibasic salt of 2,5-dihydroxyterephthalic acid with acid to form the 2,5-dihydroxyterephthalic acid product. The term "dibasic salt" as used herein denotes the salt of a dibasic acid, which is an acid that contains two replaceable hydrogen atoms per molecule.

Suitable dihaloterephthalic acids with which the process of this invention is started include 2,5-dibromoterephthalic acid, 2,5-dichloroterephthalic acid, and 2,5-diiodoterephthalic acid, or mixtures thereof. 2,5-dibromoterephthalic acid ("DBTA") is commercially available. It can, however, be synthesized, for example, by oxidation of p-xylene in aqueous hydrogen bromide (McIntyre et al, *Journal of the Chemical Society*, Abstracts, 1961, 4082-5), by bromination of terephthalic acid or terephthaloyl chloride (U.S. Pat. No. 3,894,079), or by oxidation of 2,5-dibromo-1,4-dimethylbenzene (DE 1,812,703). 2,5-dichloroterephthalic acid is also commercially available. It can, however, be synthesized, for example, by oxidation of 2,5-dichloro-1,4-dimethylbenzene [Shcherbina et al, *Zhurnal Prikladnoi Khimii* (Sankt-Peterburg, Russian Federation, 1990)], 63(2), 467-70. 2,5-diiodoterephthalic acid can be synthesized, for example, by oxidation of 2,5-diiodo-1,4-dimethylbenzene [Perry et al, *Macromolecules* (1995), 28(10), 3509-15].

In step (a), 2,5-dihaloterephthalic acid is contacted with base in water to form therefrom the corresponding dibasic salt of 2,5-dihaloterephthalic acid. In step (b), the dibasic salt of 2,5-dihaloterephthalic acid is contacted with base in water, and with a copper source in the presence of a ligand that coordinates to copper, to form the dibasic salt of 2,5-dihydroxyterephthalic acid from the dibasic salt of 2,5-dihaloterephthalic acid.

The base used in step (a) and/or step (b) may be an ionic base, and may in particular be one or more of a hydroxide, carbonate, bicarbonate, phosphate or hydrogen phosphate of one or more of Li, Na, K, Mg or Ca. The base used may be water-soluble, partially water-soluble, or the solubility of the base may increase as the reaction progresses and/or as the base is consumed. NaOH and $Na_2CO_3$ are preferred, but other suitable organic bases may be selected, for example, from the group consisting of trialkylamines (such as tributylamine); N,N,N',N'-tetramethylethylenediamine; and N-alkyl imidazoles (for example, N-methylimidazole). In principle any base capable of maintaining a pH above 8 and/or binding the acid produced during the reaction of the 2,5-dihaloterephthalic acid is suitable.

The specific amounts of base to be used in steps (a) and/or (b) depend on the strength of the base. In step (a), 2,5-dihaloterephthalic acid is preferably contacted with at least about two equivalents of base, preferably a water-soluble base, per equivalent of 2,5-dihaloterephthalic acid. One "equivalent" as used for a base in this context is the number of moles of base that will react with one mole of hydrogen ions; for an acid, one equivalent is the number of moles of acid that will supply one mole of hydrogen ions.

In step (b), enough base should be used to maintain a solution pH of at least about 8, or at least about 9, or at least about 10, and preferably between about 9 and about 11. Thus, typically in step (b), the dibasic salt of 2,5-dihaloterephthalic acid is contacted with at least about two equivalents of base, such as a water-soluble base, per equivalent of the dibasic salt of 2,5-dihaloterephthalic acid.

In alternative embodiments, however, it may be desirable in steps (a) and (b) to use a total of at least about 4 to about 5 equivalents of base, such as a water-soluble base, in the reaction mixture per equivalent of 2,5-dihaloterephthalic acid originally used at the start of the reaction. A base used in an amount as described above is typically a strong base, and is typically added at ambient temperature. The base used in step (b) may be the same as, or different than, the base used in step (a).

As mentioned above, in step (b), the dibasic salt of 2,5-dihaloterephthalic acid is also contacted with a copper source in the presence of a ligand that coordinates to copper.

The copper source and the ligand may be added sequentially to the reaction mixture, or may be combined separately (for example, in a solution of water or acetonitrile) and added together. The copper source may be combined with the ligand in the presence of oxygen in water, or be combined with a solvent mixture containing water.

From the presence together in the reaction mixture of the copper source and the ligand, in a basic solution of the dibasic salt of the 2,5-dihaloterephthalic acid, there is obtained an aqueous mixture containing the dibasic salt of 2,5-dihydroxyterephthalic acid, copper specie(s), the ligand, and a halide salt. If desired, the dibasic salt of 2,5-dihydroxyterephthalic acid may, at this stage and before the acidification in step (d), be separated from the mixture [as optional step (c)], and may be used as a dibasic salt in another reaction or for other purposes.

The dibasic salt of 2,5-dihydroxyterephthalic acid is then contacted in step (d) with acid to convert it to the 2,5-dihydroxyterephthalic acid product. Any acid of sufficient strength to protonate the dibasic salt is suitable. Examples include without limitation hydrochloric acid, sulfuric acid and phosphoric acid.

The reaction temperature for steps (a) and (b) is preferably between about 60 and about 120° C., more preferably between about 75 and about 95° C.; and the process thus in various embodiments involves a step of heating the reaction mixture. The solution is typically allowed to cool before the acidification in step (d) is carried out. In various embodiments, oxygen may be excluded during the reaction.

The copper source is copper metal ["Cu(0)"], one or more copper compounds, or a mixture of copper metal and one or more copper compounds. The copper compound may be a Cu(I) salt, a Cu(II) salt, or mixtures thereof. Examples include without limitation CuCl, CuBr, CuI, $Cu_2SO_4$, $CuNO_3$, $CuCl_2$, $CuBr_2$, $CuI_2$, $CuSO_4$, and $Cu(NO_3)_2$. CuBr is preferred. The amount of copper provided is typically about 0.1 to about 5 mol % based on moles of 2,5-dihaloterephthalic acid.

When the copper source is Cu(0), Cu(0), copper bromide and a ligand may be combined in the presence of air. In the case of Cu(0) or Cu(I), a predetermined amount of metal and ligand may be combined in water, and the resulting mixture may be reacted with air or dilute oxygen until a colored solution is formed. The resulting metal/ligand solution is added to the reaction mixture containing the dibasic salt of 2,5-dihaloterephthalic acid and base in water.

The ligand may be a diketone described generally by Formula IV

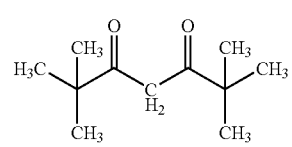

IV wherein A is

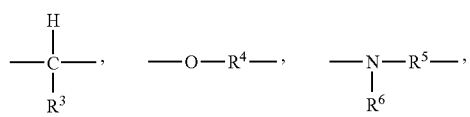

or

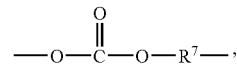

$R^1$ and $R^2$ are each independently selected from substituted and unsubstituted $C_1$-$C_{16}$ n-alkyl, iso-alkyl and tertiary alkyl groups; and substituted and unsubstituted $C_6$-$C_{30}$ aryl and heteroaryl groups;

$R^3$ is selected from H; substituted and unsubstituted $C_1$-$C_{16}$ n-alkyl, iso-alkyl and tertiary alkyl groups; substituted and unsubstituted $C_6$-$C_{30}$ aryl and heteroaryl groups; and a halogen;

$R^4$, $R^5$, $R^6$ and $R^7$ are each independently H or a substituted or unsubstituted $C_1$-$C_{16}$ n-alkyl, iso-alkyl or tertiary alkyl group; and n=0 or 1.

The term "unsubstituted", as used with reference to an alkyl or aryl group in a diketone as described above, means that the alkyl or aryl group contains no atoms other than carbon and hydrogen. In a substituted alkyl or aryl group, however, one or more O or S atoms may optionally be substituted for any one or more of the in-chain or in-ring carbon atoms, provided that the resulting structure contains no —O—O— or —S—S—moieties, and provided that no carbon atom is bonded to more than one heteroatom. n a preferred embodiment, $R^3$ is H.

In one embodiment, a diketone suitable for use herein as the ligand is 2,2',6,6'-tetramethylheptanedione-3,5 (Formula V):

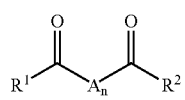

V

Other diketones suitable for use herein as the ligand include, without limitation, 2,4-pentanedione and 2,3-pentanedione.

A ligand suitable for use herein may be selected as any one or more or all of the members of the whole population of ligands described by name or structure above. A suitable ligand may, however, also be selected as any one or more or all of the members of a subgroup of the whole population, where the subgroup may be any size (1, 2, 6, 10 or 20, for example), and where the subgroup is formed by omitting any one or more of the members of the whole population as described above. As a result, the ligand may in such instance not only be selected as one or more or all of the members of any subgroup of any size that may be formed from the whole population of ligands as described above, but the ligand may also be selected in the absence of the members that have been omitted from the whole population to form the subgroup.

In various embodiments, the ligand may be provided in an amount of about 1 to about 10, preferably about 1 to about 2, molar equivalents of ligand per mole of copper. As used herein, the term "molar equivalent" indicates the number of moles of ligand that will interact with one mole of copper.

When the 2,5-dihaloterephthalic acid is 2,5-dibromoterephthalic acid, the copper source may be Cu(0) and/or a Cu(I) salt, and it may be combined with the ligand in the presence of oxygen in water, or a solvent mixture containing water. Alternatively, when the Cu(I) salt is CuBr, and the ligand is one of the diketones named specifically above (such as 2,2',6,6'-tetramethylheptanedione-3,5), the ligand may be provided in an amount of two molar equivalents per mole of copper, and the CuBr may be combined with the ligand in the presence of water and air.

The ligand is believed to facilitate the action of the copper source as a catalyst, and/or the copper source and the ligand are believed to function together to act as a catalyst, to improve one or more attributes of the reaction.

The process described above also allows for effective and efficient synthesis of related compounds, such as a 2,5-dialkoxy terephthalic acid, which may be described generally by the structure of Formula VI:

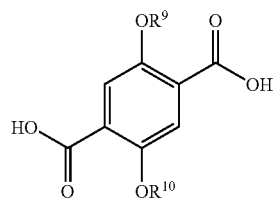

VI wherein $R^9$ and $R^{10}$ are each independently a substituted or unsubstituted $C_{1-10}$ alkyl group. $R^9$ and $R^{10}$ are, when unsubstituted, univalent groups containing only carbon and hydrogen. In any of those alkyl groups, however, one or more O or S atoms may optionally be substituted for any one or more of the in-chain carbon atoms, provided that the resulting structure contains no —O—O— or —S—S— moieties, and provided that no carbon atom is bonded to more than one heteroatom.

A 2,5-dihydroxy terephthalic acid, as prepared by the process of this invention, may be converted to a 2,5-dialkoxy terephthalic acid, and such conversion may be accomplished, for example, by contacting a 2,5-dihydroxy terephthalic acid under basic conditions with a dialkyl sulfate of the formula $R^9 R^{10} SO_4$. One suitable method of running such a conversion reaction is as described in Austrian Patent No. 265,244. Suitable basic conditions for such conversion are a solution pH of at least about 8, or at least about 9, or at least about 10, and preferably about 9 to about 11, using one or more bases such as described above.

In certain embodiments, it may be desired to separate the 2,5-dihydroxyterephthalic acid from the reaction mixture in which it was formed before converting it to a 2,5-dialkoxyterephthalic acid.

The process described above also allows for effective and efficient synthesis of products made from the resulting 2,5-dihydroxyterephthalic acid or 2,5-dialkoxyterephthalic acid such as a compound, a monomer, or an oligomer or polymer thereof. These produced materials may have one or more of ester functionality, ether functionality, amide functionality, imide functionality, imidazole functionality, carbonate functionality, acrylate functionality, epoxide functionality, urethane functionality, acetal functionality, and anhydride functionality.

Representative reactions involving a material made by the process of this invention, or a derivative of such material, include, for example, making a polyester from a 2,5-dihydroxyterephthalic acid and either diethylene glycol or triethylene glycol in the presence of 0.1% of $ZN_3(BO_3)_2$ in 1-methylnaphthalene under nitrogen, as disclosed in U.S. Pat. No. 3,047,536 (which is incorporated in its entirety as a part hereof for all purposes). Similarly, a 2,5-dihydroxyterephthalic acid is disclosed as suitable for copolymeriztion with a dibasic acid and a glycol to prepare a heat-stabilized polyester in U.S. Pat. No. 3,227,680 (which is incorporated in its entirety as a part hereof for all purposes), wherein representative conditions involve forming a prepolymer in the presence of titanium tetraisopropoxide in butanol at 200~250° C., followed by solid-phase polymerization at 280° C. at a pressure of 0.08 mm Hg.

A 2,5-dihydroxyterephthalic acid has also been polymerized with the trihydrochloride-monohydrate of tetraminopyridine in strong polyphosphoric acid under slow heating above 100° C. up to about 180° C. under reduced pressure, followed by precipitation in water, as disclosed in U.S. Pat. No. 5,674,969 (which is incorporated in its entirety as a part hereof for all purposes); or by mixing the monomers at a temperature from about 50° C. to about 110° C., and then 145° C. to form an oligomer, and then reacting the oligomer at a temperature of about 160° C. to about 250° C. as disclosed in U.S. Provisional Application No. 60/665,737, filed Mar. 28, 2005 (which is incorporated in its entirety as a part hereof for all purposes), published as WO 2006/104974. The polymer that may be so produced may be a pyridobisimidazole-2,6-diyl(2,5-dihydroxy-p-phenylene) polymer such as a poly(1,4-(2,5-dihydroxy)phenylene-2,6-pyrido[2,3-d: 5,6-d']bisimidazole)polymer, or a poly[(1,4-dihydrodiimidazo[4,5-b:4',5'-e]pyridine-2,6-diyl)(2,5-dihydroxy-1,4-phenylene)]polymer. The pyridobisimidazole portion thereof may, however, be replaced by any or more of a benzobisimidazole, benzobisthiazole, benzobisoxazole, pyridobisthiazole and a pyridobisoxazole; and the 2,5-dihydroxy-p-phenylene portion thereof may be replace the derivative of one or more of isophthalic acid, terephthalic acid, 2,5-pyridine dicarboxylic acid, 2,6-naphthalene dicarboxylic acid, 4,4'-diphenyl dicarboxylic acid, 2,6-quinoline dicarboxylic acid, and 2,6-bis(4-carboxyphenyl)pyridobisimidazole.

EXAMPLES

This invention is further defined in the following examples. These examples, while indicating preferred embodiments of the invention, are given by way of illustration only, and do not limit the scope of the appended claims. From the above discussion and these examples, the essential characteristics of this invention may be ascertained, and, without departing from the spirit and scope thereof, modifications of the invention may be made to adapt it to various uses and conditions.

Materials: The following materials were used in the examples. All reagents were used as received. Product purity was determined by $^1H$ NMR.

The 2,2',6,6'-tetramethylheptanedione-3,5 (>98% purity) was obtained from Aldrich Chemical Company (Milwaukee, Wis., USA). The 2,5-dibromoterephthalic acid (95+% purity) was obtained from Maybridge Chemical Company Ltd.(Cornwall, United Kingdom). Copper(I) bromide ("CuBr") (98% purity) was obtained from Acros Organics (Geel, Belgium). $Na_2CO_3$ (99.5% purity) was obtained from EM Science (Gibbstown, N.J.).

As used herein, the term "conversion" denotes to how much reactant was used up as a fraction or percentage of the theoretical amount. As used herein, the term "selectivity" for a product P denotes the molar fraction or molar percentage of P in the final product mix. The conversion times the selectivity thus equals the maximum "yield" of P; the actual or "net" yield will normally be somewhat less than this because of sample losses incurred in the course of activities such as isolating, handling, drying, and the like. As used herein, the term "purity" denotes what percentage of the in-hand, isolated sample is actually the specified substance.

The terms "H$_2$O" and "water" refer to distilled water. The meaning of abbreviations is as follows: "h" means hour(s), "min" means minute(s), "mL" means milliliter(s), "g" means gram(s), "mg" means milligram(s), "mol equiv" means molar equivalent(s), "mmol" means millimole(s), and "NMR" means nuclear magnetic resonance spectroscopy.

Example 1

This example demonstrates the formation of 2,5-dihydroxyterephthalic acid from 2,5-dibromoterephthalic acid using CuBr and the diketone ligand 2,2',6,6'-tetramethylheptanedione-3,5 (as shown in Formula V):

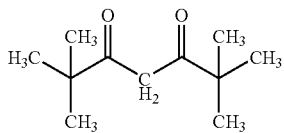

V

Under nitrogen, 2.00 g (6.2 mmol) of 2,5-dibromoterephthalic acid was combined with 15 g of H$_2$O; 0.679 g (6.4 mmol) of Na$_2$CO$_3$ was then added. The mixture was heated to reflux with stirring for 30 min, remaining under a nitrogen atmosphere. Another 0.940 g (9.0 mmol) of Na$_2$CO$_3$ was added to the reaction mixture and reflux was continued for 30 min. Separately, 9 mg (0.06 mmol) (0.01 mol equiv) of CuBr and 25 mg (0.14 mmol) (0.02 mol equiv) of 2,2',6,6'-tetramethylheptanedione-3,5 were combined with 2 mL H$_2$O under nitrogen. The resulting mixture was stirred under an air atmosphere until the CuBr was dissolved. This solution was added to the stirred reaction mixture via syringe at 80° C. under nitrogen and stirred for 30 h at 80° C. After cooling to 25° C., the reaction mixture was acidified with HCl (conc.), producing a dark yellow precipitate. The yellow precipitate was filtered and washed with water. After drying, a total of 1.26 g of crude 2,5-dihydroxyterephthalic acid and 2-hydroxyterephthalic acid was collected. The purity of 2,5-dihydroxyterephthalic acid was determined by $^1$H NMR to be about 89%. The net yield of 2,5-dihydroxyterephthalic acid was determined to be 92%.

Where an embodiment of this invention is stated or described as comprising, including, containing, having, being composed of or being constituted by certain features, it is to be understood, unless the statement or description explicitly provides to the contrary, that one or more features in addition to those explicitly stated or described may be present in the embodiment. An alternative embodiment of this invention, however, may be stated or described as consisting essentially of certain features, in which embodiment features that would materially alter the principle of operation or the distinguishing characteristics of the embodiment are not present therein. A further alternative embodiment of this invention may be stated or described as consisting of certain features, in which embodiment, or in insubstantial variations thereof, only the features specifically stated or described are present.

Where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

Where a range of numerical values is recited herein, unless otherwise stated, the range is intended to include the endpoints thereof, and all integers and fractions within the range. It is not intended that the scope of the invention be limited to the specific values recited when defining a range.

What is claimed is:

1. A process for preparing 2,5-dihydroxyterephthalic acid comprising the steps of:
   (a) contacting a 2,5-dihaloterephthalic acid, as described generally by Formula III

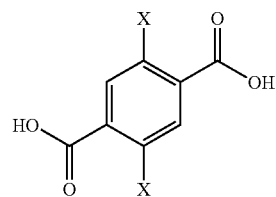

III wherein X=Cl, Br, or I, with base in water to form therefrom the corresponding dibasic salt of the 2,5-dihaloterephthalic acid;
   (b) contacting the dibasic salt of the 2,5-dihaloterephthalic acid with base in water, and with a copper source in the presence of a ligand that coordinates to copper, to form the dibasic salt of 2,5-dihydroxyterephthalic acid from the dibasic salt of 2,5-dihaloterephthalic acid at a solution pH of at least about 8; wherein the ligand comprises a diketone described generally by Formula IV

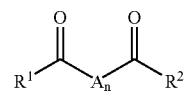

IV wherein A is

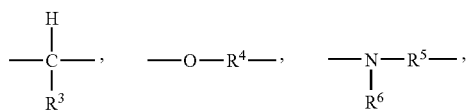

or

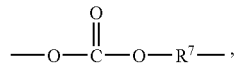

R$^1$ and R$^2$ are each independently selected from substituted and unsubstituted C$_1$-C$_{16}$ n-alkyl, iso-alkyl and tertiary alkyl groups; and substituted and unsubstituted C$_6$-C$_{30}$ aryl and heteroaryl groups;

R³ is selected from H; substituted and unsubstituted C₁-C₁₆ n-alkyl, iso-alkyl and tertiary alkyl groups; substituted and unsubstituted C₆-C₃₀ aryl and heteroaryl groups; and a halogen;

R⁴, R⁵, R⁶ and R⁷ are each independently H or a substituted or unsubstituted C₁-C₁₆ n-alkyl, iso-alkyl or tertiary alkyl group; and n=0 or 1;

(c) optionally, separating the dibasic salt of 2,5-dihydroxyterephthalic acid from the reaction mixture in which it is formed; and (d) contacting the dibasic salt of 2,5-dihydroxyterephthalic acid with acid to form therefrom 2,5-dihydroxyterephthalic acid.

2. A process according to claim 1 wherein, in step (a), the 2,5-dihaloterephthalic acid is contacted with at least about two normal equivalents of water-soluble base per equivalent of the 2,5-dihaloterephthalic acid.

3. A process according to claim 1 wherein, in step (b), the dibasic salt of the 2,5-dihaloterephthalic acid is contacted with at least about two normal equivalents of water-soluble base per equivalent of the dibasic salt of the 2,5-dihaloterephthalic acid.

4. A process according to claim 1 wherein, in steps (a) and (b), a total of about 4 to about 5 normal equivalents of water-soluble base are added to the reaction mixture per equivalent of 2,5-dihaloterephthalic acid.

5. A process according to claim 1 wherein the copper source comprises Cu(0), a Cu(I) salt, a Cu(II) salt, or a mixture thereof.

6. A process according to claim 1 wherein the copper source is selected from the group consisting of CuCl, CuBr, CuI, Cu₂SO₄, CuNO₃, CuCl₂, CuBr₂, CuI₂, CuSO₄, Cu(NO₃)₂, and mixtures thereof.

7. A process according to claim 1 wherein R³ is H.

8. A process according to claim 1 wherein the ligand is 2,4-pentanedione, 2,3-pentanedione or 2,2',6,6'-tetramethylheptanedione-3,5 (as shown below):

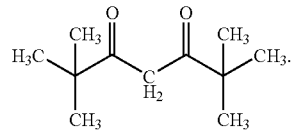

9. A process according to claim 1 further comprising a step of combining the copper source with the ligand before adding them to the reaction mixture.

10. A process according to claim 1 wherein the copper source comprises CuBr.

11. A process according to claim 1 wherein the copper source comprises CuBr; the ligand is 2,2',6,6'-tetramethylheptanedione-3,5; the ligand is provided in an amount of two molar equivalents per mole of copper; and the CuBr is combined with the ligand in the presence of water and air.

12. A process according to claim 1 wherein a base comprises one or more of a water-soluble hydroxide, phosphate, carbonate, or bicarbonate of one or more of Li, Na, K, Mg, or Ca.

13. A process according to claim 1 wherein a base comprises NaOH or Na₂CO₃.

14. A process according to claim 1 wherein copper is provided in an amount of between about 0.1 and about 5 mol % based on moles of 2,5-dihaloterephthalic acid.

15. A process according to claim 1 wherein the ligand is provided in an amount of between about one and about two molar equivalents per mole of copper.

* * * * *